Figure 1:
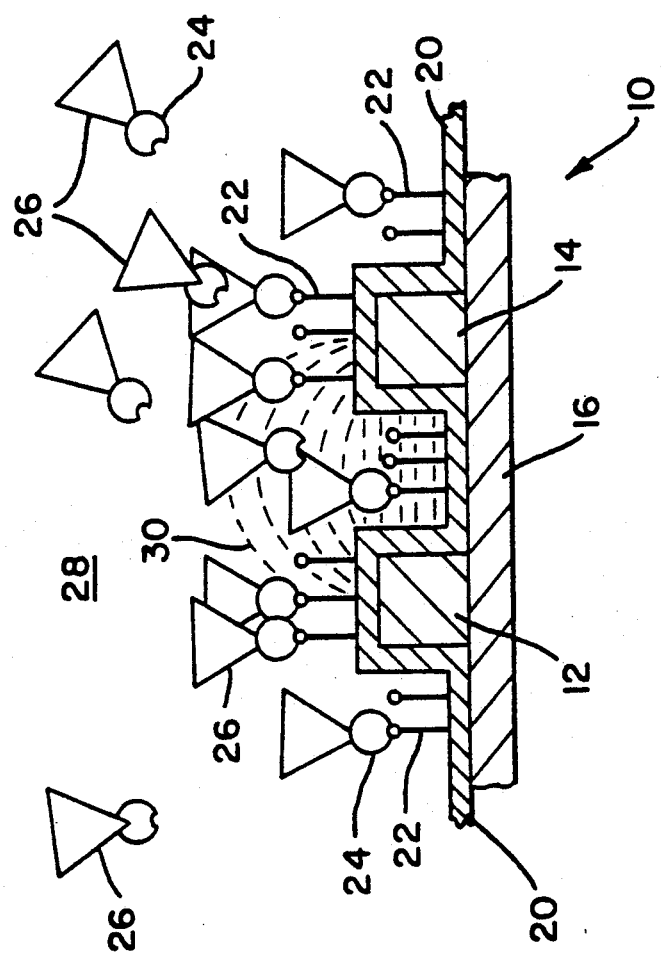

US005114674A

United States Patent [19]

Stanbro et al.

[11] Patent Number: 5,114,674
[45] Date of Patent: May 19, 1992

[54] ADDED ARRAY OF MOLECULAR CHAINS FOR INTERFERING WITH ELECTRICAL FIELDS

[75] Inventors: William D. Stanbro, Columbia; Kenneth W. Hunter, Jr., Potomac; Arnold L. Newman, Kensington, all of Md.

[73] Assignee: Biotronic Systems Corporation, Rockville, Md.

[21] Appl. No.: 44,767

[22] Filed: May 1, 1987

[51] Int. Cl.$^5$ .................... G01N 27/02; G01N 33/345

[52] U.S. Cl. .................................. 422/57; 204/153.1; 204/403; 422/82.02; 436/525

[58] Field of Search .................. 422/69, 79, 82.02, 57; 204/1 T, 403, 14.1, 35.1, 153.1; 436/500, 525, 63, 149, 806

[56] References Cited

U.S. PATENT DOCUMENTS

| | | | |
|---|---|---|---|
| 4,072,576 | 2/1978 | Arwin et al. . | |
| 4,092,116 | 5/1978 | Giaever . | |
| 4,238,757 | 12/1980 | Schenck . | |
| 4,453,126 | 6/1984 | Volgyesi . | |
| 4,490,216 | 12/1984 | McConnell . | |
| 4,562,157 | 12/1985 | Lowe et al. | 435/291 |
| 4,571,543 | 2/1986 | Raymond et al. | 422/98 |
| 4,637,861 | 1/1987 | Krull et al. . | |
| 4,713,347 | 12/1987 | Mitchell et al. | 436/501 |

FOREIGN PATENT DOCUMENTS

| | | |
|---|---|---|
| 0150999 | 8/1985 | European Pat. Off. . |
| 2599844 | 12/1987 | France . |

OTHER PUBLICATIONS

"Adsorption Of Blood Proteins On Metals Using Capacitance Techniques", by Stoner et al., The Journal of Physical Chemistry, vol. 74, No. 5, Mar. 5, 1970.

*Primary Examiner*—Jill A. Johnston
*Attorney, Agent, or Firm*—Kerkam, Stowell, Kondracki & Clarke

[57] ABSTRACT

An array of molecular chains is added to a dielectric material between two electrodes of a capacitive affinity sensor. Such an array of molecular chains greatly changes dielectric properties between the two electrodes to greatly enhance sensitivity of the sensor. In a sensor using direct binding, a viral fragment is bound to the sensor's surface. A molecular chain, comprising an anti-viral antibody, an anti-human antibody, and a protein molecule, binds to the viral fragment. In a sensor using competitive binding a hapten is bound to the sensor's surface. A molecular chain, comprising an antibody with attached aliphatic hydrocarbons, binds to the hapten. A free analyte competes with the hapten to bind with the antibody.

29 Claims, 4 Drawing Sheets

ADDED ARRAY OF MOLECULAR CHAINS FOR INTERFERING WITH ELECTRICAL FIELDS

BACKGROUND OF THE INVENTION

Cross reference is made to two U.S. patent applications: Ser. No. 044/761, now U.S. Pat. No. 5,082,627 for Three Dimensional Binding Site Array For Interfering With An Electrical Field, by W. D. Stanbro; and Ser. No. 044,769, now U.S. Pat. No. 4,769,121 for Sintered Pellet With Biochemically Active Layer, by A. L. Newman, which were filed the same date and were assigned to the same entity as this application.

The invention relates to a means for interfering with an electrical field. More specifically, the invention relates to an electrode insulated with an added array of molecular chains.

In composition analysis, capacitive sensors have been used to determine the concentration of a specific gas in a mixture, or an analyte in a fluid, for example. Such sensors measure a capacitance that changes with that concentration.

Newman U.S. patent application Ser. No. 799,761, filed Nov. 19, 1985, and now abandoned, ("the Newman Patent Application") involves a capacitor for determining the concentration of an analyte in a fluid, for instance. Biospecific binding reactions occur in a space between electrodes of a capacitive sensor. These reactions occur among molecules of a binding agent immobilized on a surface and an analyte in a fluid. These reactions result in the displacement of small fluid molecules having high dielectric constants by large biochemical molecules having low-dielectric constants. This displacement of molecules changes the dielectric properties of the capacitor.

Raymond et al. U.S. Pat. No. 4,571,543 discusses a capacitor for detecting and measuring the concentration of specific non-aqueous materials or constituents in fluids. The capacitor is layered with a coating of silane and then a coating of certain polymers. These polymers form membranes that are permeable to constituents of the fluids. The constituents penetrate through the membrane to change the dielectric constant of a solution in the membrane.

Volgyesi U.S. Pat. No. 4,453,126 concerns a capacitor for monitoring the concentration of anaesthetic gas in a breathing mixture. The capacitor has a dielectric of lipids or elastomers which permit the absorption of the anaesthetic gas to vary electrical characteristics of the sensor.

"Adsorption Of Blood Proteins On Metals Using Capacitance Techniques", by Stoner et al., The Journal of Physical Chemistry, Vol. 74, No. 5, Mar. 5, 1970, describes a differential capacity method for measuring adsorption of proteins on solid metal electrodes.

Arwin et al. U.S. Pat. No. 4,072,576 relates to a capacitive method for studying enzymatic activity and for studying an immunological reaction. An adsorbed polypeptide substrate is used in studying enzymatic activity and an antigen is adsorbed onto an electrode surface in studying the reaction of the antigen with an antibody.

SUMMARY OF THE INVENTION

The invention concerns an apparatus, and a method for making the apparatus, comprising a base layer, an electrical field generating means on the base layer, and an electrical field interfering means. The electrical field interfering means has a biochemically active layer comprising an antigen or an antibody, and a molecular chain that extends from the biochemically active layer, for instance. In one version, the molecular chain comprises another antibody and a protein molecule. In another version, the molecular chain comprises an alkyl or an amide molecule.

In a specific embodiment, the electrical field generating means is an electrode of a capacitive affinity sensor, for instance. In this embodiment, the biochemically active layer is part of a dielectric material between electrodes of the sensor, where the molecular chains bind. Thus, the thickness of the dielectric material greatly increases and the capacitance of the biochemically active layer greatly decreases. Such a biochemically active layer is used to provide a very sensitive capacitive affinity sensor, for instance.

BRIEF DESCRIPTION OF THE FIGURES

FIG. 1 shows electrodes of a capacitive affinity sensor with a dielectric material according to this invention.

FIG. 2 schematically shows direct binding of an array of molecular chains according to this invention.

FIG. 3 shows another version of the molecular chain of FIG. 2.

FIG. 4 shows competitive binding of an array of molecular chains.

FIGS. 5 and 6 show examples of molecular chains for a competitive binding array.

DETAILED DESCRIPTION

Capacitive affinity sensors measure the concentration of an analyte by detecting a change in capacitance as an analyte molecule moves in or out of an electric field between two electrodes of the sensor, for instance. The moving analyte molecule has a low dielectric constant and displaces solvent molecules having higher dielectric constants from a biochemically active layer between the two electrodes. The displacement of the solvent molecules by the analyte molecules reduces capacitance between the two electrodes. The capacitance between the two electrodes is inversely proportional to the concentration of the analyte being measured by such a sensor.

Other capacitances are present in a capacitive affinity sensor and include the capacitance of any passivating layers over the electrodes and the capacitance of the solvent about the electrodes. The capacitances of the sensor add as follows:

$$C_T = \frac{1}{\sum_{i=1}^{n} \frac{1}{C_i}} \quad (1)$$

where $C_T$ is the total capacitance of the sensor and $C_i$ is the capacitance of each of the biochemically active layer, the passivating layer and of the solvent. For an idealized parallel plate capacitor, the individual capacitances are proportional to the ratio of the dielectric constant and the distance between the parallel plates. That is $$C_i \propto \frac{\epsilon_i}{d_i} \quad (2)$$

where $\epsilon_i$ is the dielectric constant and $d_i$ is the distance between the parallel plates. This type of situation applies regardless of the actual geometry of the plates.

A passivating layer of a capacitive affinity sensor is about 2000 Angstroms thick and provides an impervious pin hole free barrier to water and ions. A solvent layer can be several microns thick. However, in a sensor as discussed in the Newman patent application, antibodies extend about 100 Angstroms above an insulator surface in the biochemically active layer. Thus, such a biochemically active layer is thin compared to the passivating layer and the solvent layer.

According to equation (2) the capacitance of such a thin, biochemically active layer is large compared to that of any passivating and solvent layers. According to equation (1) the dominant capacitance in the total capacitance $C_T$ is that of the layer having the lowest capacitance. Thus, it is desirable to minimize the capacitance of the layer of an affinity sensor that is modulated, such as the biochemically active layer, to maximize the sensitivity of such a sensor. Minimizing the capacitance of the biochemically active layer brings the capacitance of this layer into the ranges of the other capacitances in the sensor.

According to equation (2), capacitance of the biochemically active layer decreases with a decrease in the dielectric constant of the layer or an increase in the thickness of the layer. The inventors have recognized that this capacitance is also affected by any molecules that might bind to the biochemically active layer, and that larger, low dielectric analyte molecules will displace a greater amount of the high dielectric solvent. The inventors have, therefore, developed a means for increasing the thickness of the dielectric material of a capacitive affinity sensor by binding large molecular chains to a biochemically active layer between electrodes of that sensor. The large molecular chains bind and displace a greater amount of solvent, which increases the difference between capacitances that are measured when all the molecular chains enter the electric field and when all leave the electric field.

FIG. 1 shows schematically a capacitive affinity sensor 10 with electrodes 12 and 14 insulated according to this invention. The sensor 10 has a base layer 16 that supports the two electrodes 12 and 14, which have opposite polarities. The base layer 16 comprises a substrate of insulating material like alumina.

A passivating layer 20 covers the base layer 16 and electrodes 12 and 14 in the preferred embodiment of this invention. The passivating layer 20 protects the electrodes 12 and 14 from water and ions in a solvent 28.

Molecules form receptors 22 that extend from the passivating layer 20. These receptors 22 form a layer that is biochemically active. Each receptor 22 of this layer is a potential binding site for a molecule of a specific analyte 24. Also, molecules of the analyte 24 can be displaced, as described below.

The receptors 22 can comprise an antibody and the analyte 24 can comprise a bacteria, for instance. In another version, the receptors 22 can comprise antigens and the analyte 24 can comprise an antibody. Though not shown, the receptors 22 also extend horizontally from any vertical surfaces covered by the passivating layer 20.

Large molecules 26 bind to the analyte 24. The large molecule 26 may comprise a protein, for instance. The analyte 24 and the large molecules 26 form large molecular chains that bind to the receptor 22 as an added array in an electric field 30 between the electrodes 12 and 14. These large molecular chains have low dielectric constants and displace a great amount of high dielectric constant solvent 28 from the electric field 30. These large molecular chains bind as an array that greatly increases the thickness $d_i$ of the dielectric material in a capacitive affinity sensor and greatly changes the dielectric properties of that sensor. According to equation (1), the capacitance between electrodes 12 and 14 greatly decreases.

FIG. 1 shows molecular chains adjacent the electrodes 12 and 14. The molecular chains are adjacent the electrodes 12 or 14 when the molecular chains substantially interfere with the electric field of such an electrode.

FIGS. 2 and 3 show embodiments of the invention which are ideal for a capacitive affinity sensor using direct binding. A capacitive affinity sensor using direct binding is described in the Newman patent application.

FIG. 2 schematically shows a detail of one array of large molecular chains 32. A sensor surface 34 comprises the base layer 16 and the passivating layer 20 of FIG. 1. A viral fragment 36 extends from the sensor surface 34 in a biochemically active layer, and is one example of the receptor molecule 22 of FIG. 1. A human anti-viral antibody 38 is an example of an analyte in the solvent 28 and is biospecific to the viral fragment 36 to bind to that fragment. An anti-human antibody 40, from a non-human animal, and a bound protein molecule 42 are added to the solvent 28. Such a protein molecule 42 has a molecular weight on the order of one million.

The anti-human antibody 40 is an antibody to the human antiviral antibody 38. A number of anti-human antibodies 40 bind to each human anti-viral antibody 38. Antibodies 38 and 40, and protein molecule 42 form a large molecular chain that binds to the viral fragment 36 on the sensor surface 34. In another version, the viral fragment 36 can also comprise a hapten that is biospecific to the human anti-viral antibody 38.

In this version of the invention, a protein molecule 42, such as thyroglobulin, is bound to the anti-human antibody 40 before both are added to the solvent 28. Thyroglobulin binds to the anti-human antibody 40 through a linker group, such as succinic acid, in a solvent of phosphate buffered saline having a pH of 6.4. 1-ethyl-3-(3)-dimethylaminopropyl (carbodiimide), known as EDC, catalyses a reaction in the solvent. Through this reaction, two carboxylic acid groups on the succinic acid bind to amine groups of the antibody 40 and of the thyroglobulin. This forms an amide linkage between the antibody 40 and the thyroglobulin. Dialysis against the phosphate buffered saline recovers the thyroglobulin and bound antibody 40. The chemical formula:

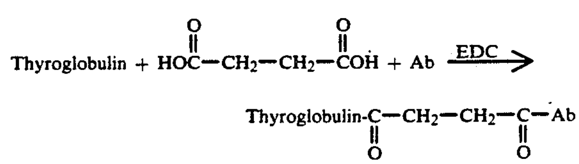

illustrates this procedure. Ab represents the antibody 40.

Many such large molecular chains form an array that is adjacent a single electrode 12 or 14 of FIG. 1. Such an array of large molecular chains forms an electrical insulator against the electric field of that single electrode. However, in a preferred version, the array of large molecular chains bind through an analyte molecule of that chain to a receptor as part of a dielectric material between the two electrodes 12 and 14 of the affinity sensor 10 of FIG. 1, for instance.

The molecular chains 32 are very large, have low dielectric constants, and, therefore, displace a great amount of the solvent 28 which has a high dielectric constant. The dielectric properties of such a sensor vary greatly with the concentration of analyte molecules, such as the antiviral antibody 38, in the solvent 28.

Figure 2:
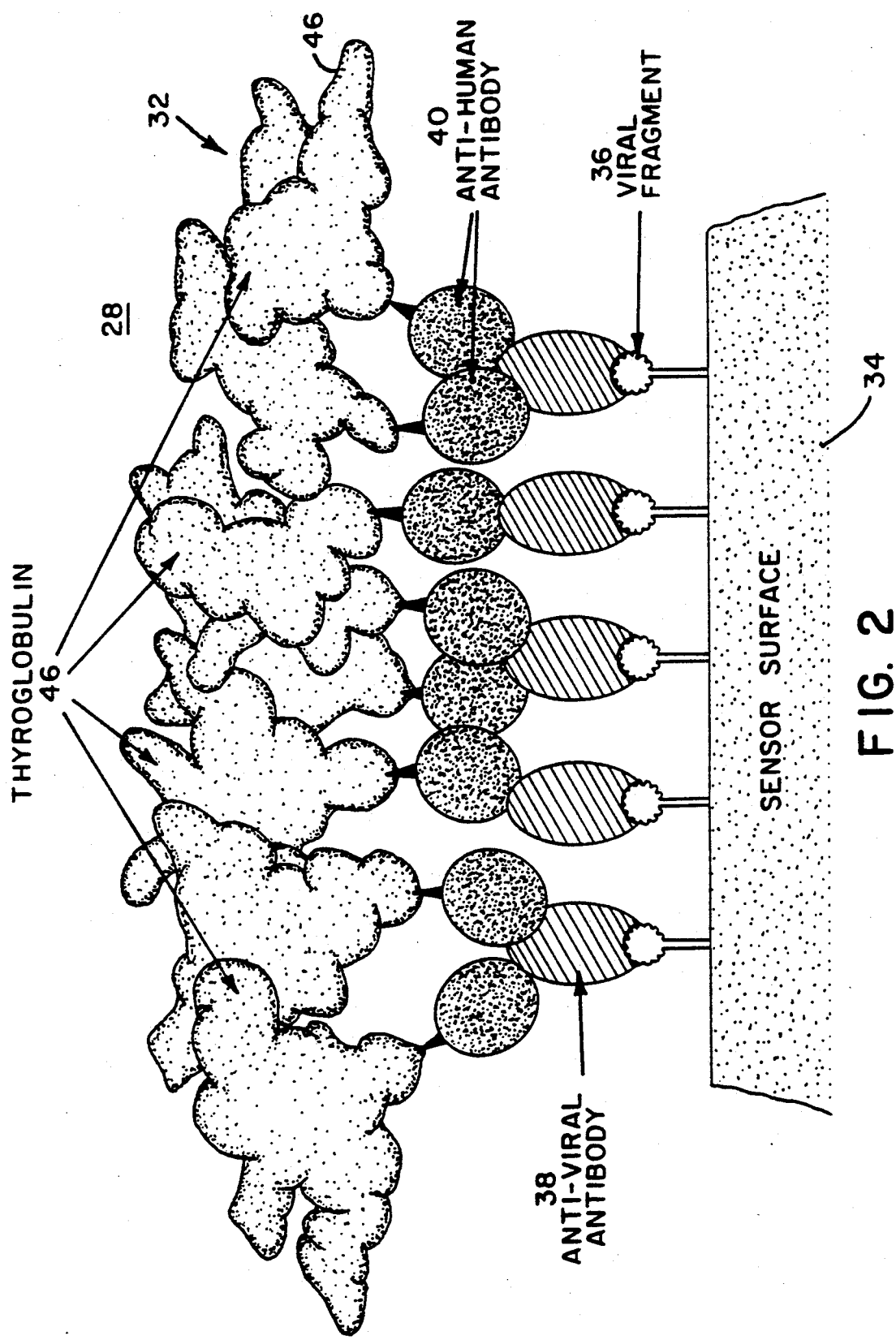
Figure 3:
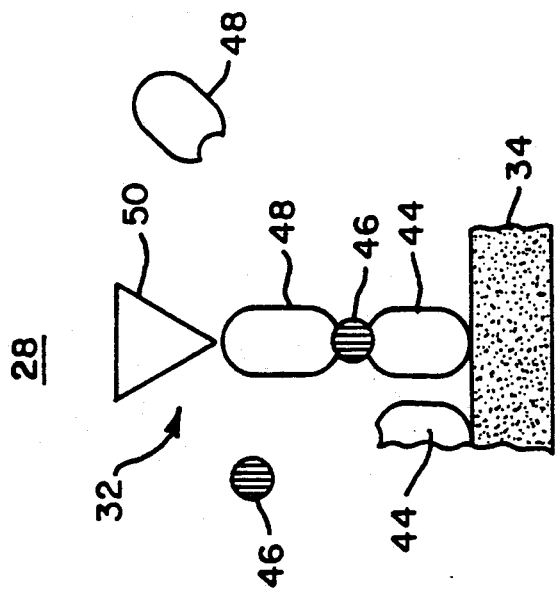

FIG. 3 shows another version of the invention shown in FIG. 2. An antibody 44 is bound directly to the sensor surface 34. Such antibodies 44 form a biochemically active layer and are biospecific to an analyte 46, like a bacteria, in the solution 28. The analyte 46 diffuses through the solution 28 until the analyte 46 binds to the antibody 44. Another antibody 48 and a bound protein molecule 50 diffuse through the solution 28 and bind atop the analyte 46. The protein molecule 50 is covalently bound to the second antibody 48 before both are added to the solution 28. These antibodies 44 and 48 can be different or the same, though each will bind to the analyte 46 through individual epitopes of this bacteria.

The antibody 48, analyte 46 and protein 50 molecules form a large molecular chain 32 that binds to the antibody 44 on the sensor surface 34. Such a large molecular chain is added in an array that interferes with the electrical field of the electrode 12 or 14 of FIG. 1, for instance.

Figure 4:
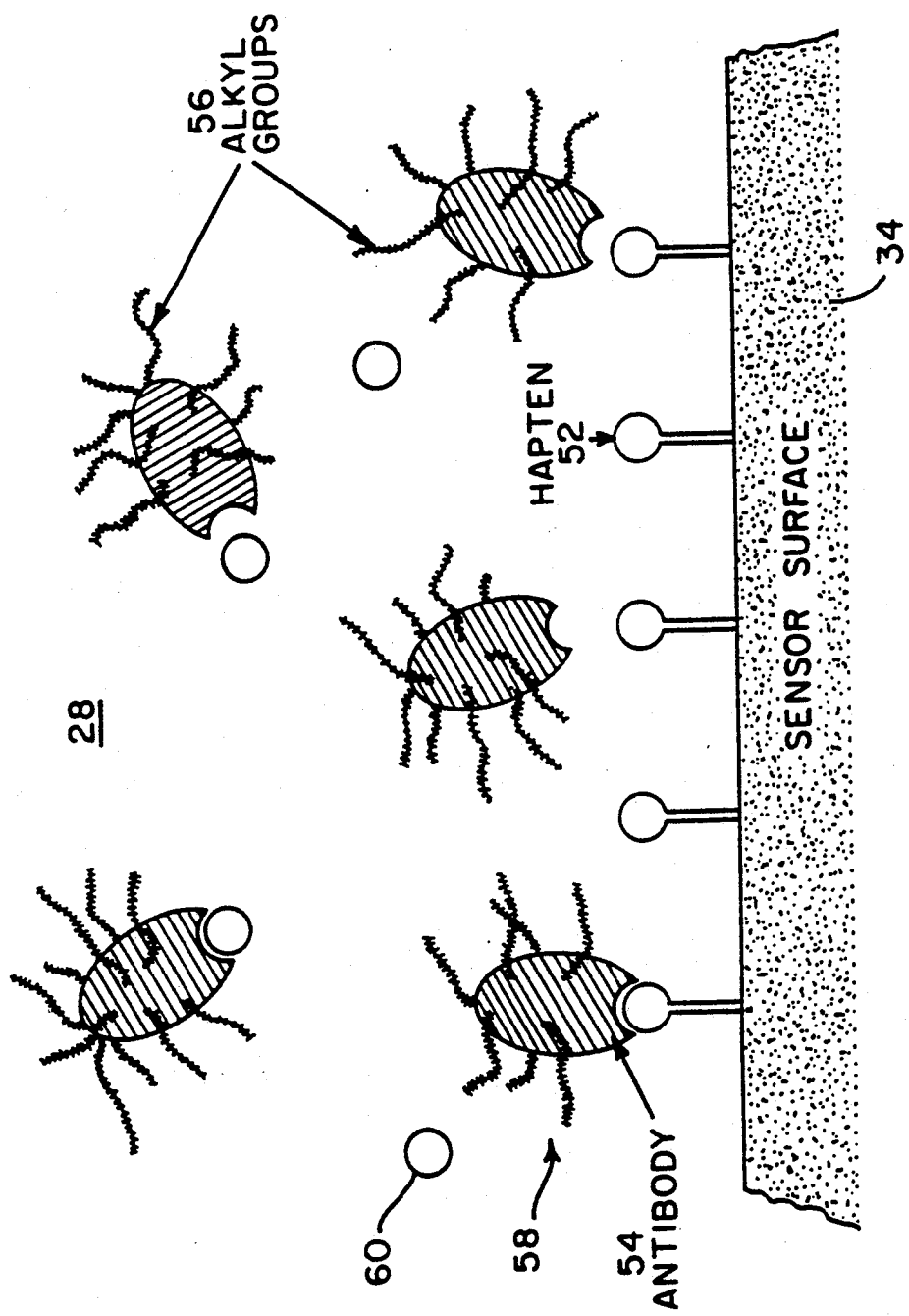

FIG. 4 shows another embodiment of the invention which is ideal for a capacitive affinity sensor using competitive binding. A capacitive affinity sensor using competitive binding is described in the Newman patent application.

A hapten 52 is an example of a receptor molecule 22 and is bound directly to the sensor surface 34. Such hapten 52 form a biochemically active layer. An antibody 54 is biospecific to and binds to the hapten 52. According to the invention, a number of aliphatic hydrocarbons or alkyl molecules 56 extend from each antibody 54.

A large molecular chain 58 comprises an antibody 54 and the alkyl molecules that extend from that antibody. This large molecular chain 58 binds to the hapten 52 of the biochemically active layer of hapten 52. Such large molecular chains 58 bind in an array as part of the dielectric material in a capacitive affinity sensor, adjacent the electrodes 12 and 14 of FIG. 1, for instance. A high dielectric constant solvent 28 covers each low dielectric constant molecular chain 58.

A free analyte 60 is introduced into the solvent 28. The analyte 60 diffuses toward the sensor surface 34. The antibodies 54 are biospecific, not only to the hapten 52, but also to the analyte 60. Thus, the hapten 52 and the analyte 60 compete to bind with an antibody 54 of a large molecular chain 58. As a result, these large molecular chains 58 diffuse through the solvent 28 away from the sensor surface 34 to bind with the free analyte 60. The amount of molecular chains 58 that diffuse through the solvent 28 from hapten 52 is proportional to the concentration of the free analyte 60 in the solvent 28.

A large volume of high dielectric constant solvent 28 replaces the low dielectric constant molecular chains 58 that diffuse from the sensor surface 34. In this way, the capacitance greatly increases between the two electrodes 12 and 14 of FIG. 1, for instance.

Figure 5:
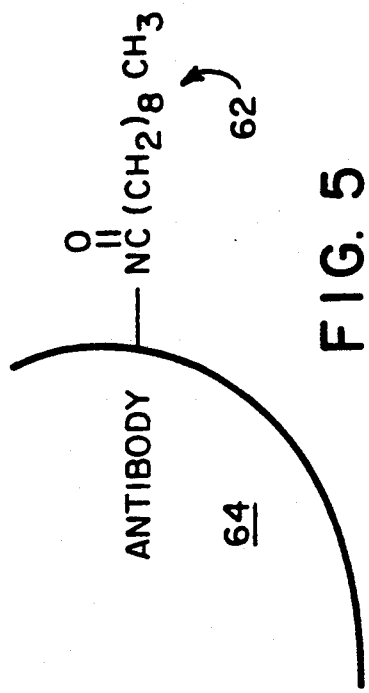

FIG. 5 shows a large amide molecular chain for use in the embodiment of FIG. 4. FIG. 5 shows an aliphatic hydrocarbon 62 extending from an antibody 64 through EDC catalyzed acylation of an amine. As an example of an aliphatic hydrocarbon 62, a decyl amide extends from the antibody 64. This amide extends through its carboxylic functional group from the terminal end of an amine group molecule, like a peptide, of the antibody 64. Instead of the peptide, the amide can bind to the side chain $(CH_2)_4NH$ of a lysine molecule in the antibody 64, for instance.

The aliphatic hydrocarbon 62 binds to the antibody 64 to form a large molecular chain, according to the following procedure. First, the antibody 64 is placed in a solution of phosphate buffered saline having a pH of 6.4. Next, EDC and decanoic acid are added to the solution. Decanoic acid is commercially available from Aldrich, No. 15,376-1. The antibody, saline, EDC, and acid may be added together in any order. After the solution reacts, the derivatized antibody is recovered by dialysis against the phosphate buffered saline to remove unreacted substances, byproducts and reagents from the solution.

The chemical formula

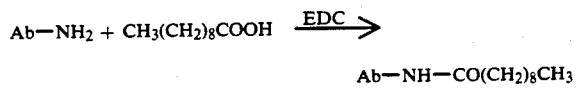

illustrates this procedure. $Ab-NH_2$ represents the antibody 64 with part of an amino group, like the terminal end of a peptide, extending from the antibody 64.

Figure 6:
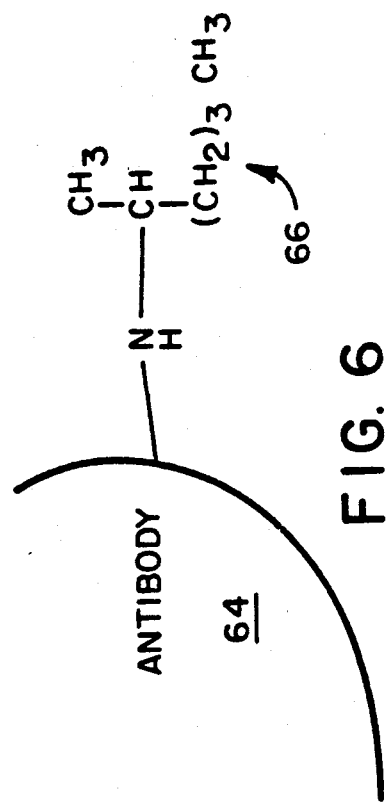

FIG. 6 shows a large alkyl molecular chain for use in the embodiment of FIG. 4. Specifically, FIG. 6 shows an alkyl group, hexcyl group molecule 66, extending from the antibody 64 through reductive alkylation. As an example, a ketone, like the 2-hexanone of FIG. 6, is bound to the terminal end of an amino group, like a peptide, of the antibody 64. Instead of the peptide, the ketone can bind to the side chain of a lysine molecule of the antibody. Also, instead of the ketone, an aldehyde can bind to a peptide or a lysine molecule of the antibody.

The alkyl group molecule 66 binds to the antibody 64 to form a large molecular chain according to the following procedure. First, the antibody is placed in a solution of phosphate buffered saline at 0 degrees Centigrade with 0.1% ethylenediaminetetraacedic acid (EDTA) and solid sodium cyanoborohydride is added as a reducing agent. Next, 2-hexanone is slowly added to the solution and is gently stirred. 2-hexanone is commercially available from Aldrich, No. 10,300-4. After the solution has reacted, the derivatized antibody is recovered by dialysis against the phosphate buffered saline to remove unreacted substances, byproducts and reagents from the solution. The chemical formula

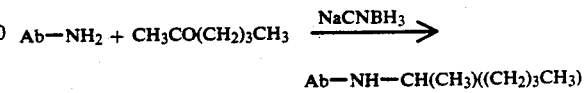

illustrates this procedure. $Ab-NH_2$ represents the antibody 64 with part of an amino group, like the terminal end of a peptide, extending from the antibody.

According to the preferred version of this invention, molecular chains add in an array to a biochemically active layer. This array thickens a dielectric material of a capacitive affinity sensor and drastically affects the dielectric properties of the sensor. The array enhances the sensitivity of the sensor to an analyte in a solution, for example.

What is claimed is:

1. An apparatus for detecting an analyte comprising:
a means for generating an electrical field;
a means for interfering with the electrical field comprising a biochemically active layer to which an analyte binds and which is adjacent the means for generating the electrical field; and
a means for enhancing interference with the electrical field according to a concentration of the analyte, and comprising a molecular chain which binds to and extends from the analyte.

2. The apparatus of claim 1, the biochemically active layer comprising a receptor molecule bound to the base, and the analyte comprising a ligand that is biospecific to the receptor molecule.

3. The apparatus of claim 2, the molecular chain comprising a protein molecule bound to the ligand.

4. The apparatus of claim 2, the ligand comprising a first antibody and the molecular chain comprising a second antibody that is an antibody to the first antibody.

5. The apparatus of claim 4, the molecular chain comprising a protein molecule bound to the second antibody.

6. The apparatus of claim 2, the molecular chain comprising an alkyl group molecule bound to the ligand.

7. The apparatus of claim 2, the molecular chain comprising an amide group molecule bound to the ligand.

8. The apparatus of claim 7, the biochemically active layer comprising a first antibody bound to the base, the analyte comprising a hapten biospecific to the first antibody, and the molecular chain comprising a second antibody biospecific to the analyte.

9. The apparatus of claim 8, the molecular chain comprising a protein molecule bound to the second antibody.

10. The apparatus of claim 8, the first and second antibodies comprising different antibodies.

11. The apparatus of claim 1 comprising a capacitive affinity sensor;
the ligand comprising a first antibody;
the means for generating comprising two electrodes between which the electric field is generated;
the means for interfering with the electrical field comprising a dielectric material between the two electrodes.

12. The apparatus of claim 11, the biochemically active layer comprising a hapten, the first antibody biospecific to the hapten, the molecular chain comprising a protein that is biospecific to the first antibody.

13. The apparatus of claim 11, the molecular chain comprising a second antibody that is an antibody to the first antibody, and a protein bound to the second antibody.

14. The apparatus of claim 11, the molecular chain comprising: an antigen that is biospecific to the first antibody; a second antibody that is biospecific to the antigen; and a protein bound to the second antibody.

15. The apparatus of claim 11, the molecular chain comprising an alkyl group molecule bound to the first antibody that is biospecific to the receptor molecule.

16. The apparatus of claim 11, the molecular chain comprising an amide group molecule bound to the first antibody that is biospecific to the receptor molecule.

17. An apparatus for detecting an analyte comprising:
a means for generating an electrical field;
a means for interfering with the electrical field comprising a biochemically active layer adjacent the means for generating the electrical field and a displaceable biochemical molecule extending from the biochemically active layer and biospecific to the biochemically active layer; and
a means for enhancing interference with the electrical field and comprising a molecular chain bound to the biochemical molecule and extending away from the biochemically active layer, wherein
the molecular chain and biochemical molecule are displaced from the biochemically active layer and change the electric field according to the concentration of an analyte.

18. The apparatus of claim 17, the biochemically active layer comprising a receptor molecule bound to the base, and the biospecific molecule comprising a ligand that is biospecific to the receptor molecule.

19. The apparatus of claim 18, the molecular chain comprising a protein molecule bound to the ligand.

20. The apparatus of claim 18, the ligand comprising a first antibody, and the molecular chain comprising a second antibody that is an antibody to the first antibody and a protein molecule bound to the second antibody.

21. The apparatus of claim 18, the molecular chain comprising an alkyl group molecule bound to the ligand.

22. The apparatus of claim 18, the molecular chain comprising an amide group molecule bound to the ligand.

23. The apparatus of claim 17, the biochemical molecule comprising a first antibody, and the molecular chain comprising: a second antibody different from the first antibody; an antigen biospecific to the first antibody and to the second antibody; and a protein molecule bound to the second antibody.

24. The apparatus of claim 17 comprising a capacitive affinity sensor;
the ligand comprising a first antibody;
the means for generating comprising two electrodes between which the electric field is generated;
the means for interfering with the electrical field comprising a dielectric material between the two electrodes.

25. The apparatus of claim 23, the biochemically active layer comprising a receptor molecule, the molecular chain comprising a first antibody biospecific to the receptor molecule and a protein bound to the first antibody.

26. The apparatus of claim 24, the molecular chain comprising a second antibody that is an antibody to the first antibody and a protein bound to the second antibody.

27. The apparatus of claim 24, the molecular chain comprising: an antigen that is biospecific to the first antibody; a second antibody that is biospecific to the antigen; and a protein bound to the second antibody.

28. The apparatus of claim 24, the molecular chain comprising an alkyl group molecule bound to the first antibody.

29. The apparatus of claim 24, the molecular chain comprising an amide group molecule bound to the first antibody.

* * * * *